United States Patent
Qiao et al.

(10) Patent No.: US 8,008,913 B2
(45) Date of Patent: Aug. 30, 2011

(54) AUTOMATIC LIFT-OFF COMPENSATION FOR PULSED EDDY CURRENT INSPECTION

(75) Inventors: Xiaoyu Qiao, Hatfield (GB); John Hansen, Harpenden (GB)

(73) Assignee: GE Inspection Technologies, Ltd, St. Albans, Hertfordshire (GB)

( * ) Notice: Subject to any disclaimer, the term of this patent is extended or adjusted under 35 U.S.C. 154(b) by 532 days.

(21) Appl. No.: 12/134,317

(22) Filed: Jun. 6, 2008

(65) Prior Publication Data

US 2008/0309328 A1 Dec. 18, 2008

(51) Int. Cl.
*G01R 33/12* (2006.01)
*G01B 5/28* (2006.01)

(52) U.S. Cl. ........ 324/225; 324/227; 324/233; 324/237; 702/38

(58) Field of Classification Search .......... 324/225–248; 702/38
See application file for complete search history.

(56) References Cited

U.S. PATENT DOCUMENTS

| | | | | |
|---|---|---|---|---|
| 4,303,885 A | * | 12/1981 | Davis et al. | 324/237 |
| 4,383,218 A | * | 5/1983 | Hansen et al. | 324/225 |
| 4,620,152 A | * | 10/1986 | Bains, Jr. | 324/225 |
| 5,371,461 A | * | 12/1994 | Hedengren | 324/225 |
| 5,391,988 A | | 2/1995 | Kitagawa | |
| 5,394,084 A | * | 2/1995 | Snyder | 324/225 |
| 6,344,741 B1 | | 2/2002 | Giguere et al. | |
| 6,573,712 B2 | | 6/2003 | Arai | |
| 2002/0093330 A1 | * | 7/2002 | Crouzen et al. | 324/240 |

FOREIGN PATENT DOCUMENTS

CA 2 312 101 12/2001

OTHER PUBLICATIONS

German Patent Application No. 102008002883.5-52, German Search Report and Written Opinion, Apr. 14, 2011.

* cited by examiner

*Primary Examiner* — Ha Tran T Nguyen
*Assistant Examiner* — Emily Y Chan
(74) *Attorney, Agent, or Firm* — Mark A. Conklin; Global Patent Operation

(57) ABSTRACT

Variations in the lift-off separation between a probe and the surface of a structure to be tested often mask the detection of defects in the structure. A method and apparatus for automatically classifying and compensating for variations in the lift-off is described. A reference signal at a known lift-off may be weighted by a corresponding calculated ratio parameter and subtracted from a test signal to compensate for lift-off. A number of reference signals are preferably obtained and the largest magnitude gradient for each reference signal is preferably determined. The largest magnitude gradient for subsequent test signals is also obtained and the corresponding reference signal with the closest largest magnitude gradient to the test signal is identified and the corresponding reference signal is selected in the related compensation procedure. Such a method has been found to restore the signal such that lift-off is removed and defects are easily identified.

12 Claims, 7 Drawing Sheets

C-Scan PEC Imaging without lift-off compensation

FIG. 5c

C-Scan PEC Imaging with lift-off compensation

AUTOMATIC LIFT-OFF COMPENSATION FOR PULSED EDDY CURRENT INSPECTION

FIELD OF THE INVENTION

The present invention relates to a method and an apparatus which may be used to detect defects such as corrosion, cracks etc in material or structures, in particular conductive structures such as aircraft panels and pipelines for example.

BACKGROUND OF THE INVENTION

Defects such as corrosion, cracks etc weaken the structural integrity of a material or structure. The failure of a structure in many industries may have very serious consequences such as the failure of a structure forming a component of a pipeline, such as a gas or oil pipeline or an aircraft panel. Consequently, considerable effort is directed to the inspection of structures to determine whether they have or acquire any defects which may affect their structural integrity.

Structures can be visually inspected in an attempt to detect defects. However, whilst some defects may be able to be detected visually, such as serious corrosion which may result in surface distortion, many defects, such as cracks or corrosion which is not easily visible from the outside surface of the structure may be missed. Furthermore, many structures are covered in layers of paint, coatings and insulation which would make visual inspection even more difficult.

Another method of inspecting structures to detect defects involves ultrasonic waves. However, ultrasonic waves can only penetrate a single layer of a structure unless subsequent layers are mechanically bonded together. Thus, defects in multilayer structures are difficult to detect.

Another method of detecting defects in structures uses eddy currents. Eddy current inspection offers important advantages for the detection of flaws in conductive structures and has a very broad range of applications. It is non-destructive, and can detect flaws invisible to the unaided eye. A single frequency is commonly used to realize non-destructive inspection. Sometimes two frequencies or multi frequencies may be used in order to improve inspection capability and detection reliability. Eddy currents can penetrate multi-layers of material to discover hidden damage which may threaten the serviceability of a material or structure. However, for precisely locating a defect position in a complex structure, conventional eddy current techniques encounter difficulties caused by frequency attenuation. A Pulsed Eddy Current (PEC) square wave pulse provides wide band frequency energy, particularly at low frequencies. Therefore it provides more information regarding defect depth and the potential for subsequent data processing.

Probe lift-off is a problem associated with passing a probe over a surface of a structure to be tested in that variations in the spacing between the probe and the structure to be inspected produce false variations in the received signal which may mask variations indicative of real defects which is misleading for the identification of defects. The variations in the lift-off may be produced, for example, by variations in the structure surface over which a probe is passed such as paint and/or coating thickness, the presence of surface features such as rivets and the variation in pressure applied to the probe by the operator when in use.

U.S. Pat. No. 6,344,741 and CA 2 312 101 disclose a method for compensating for lift-off variations in pulsed eddy current techniques. Calibration signals are obtained from a probe at two or more different lift-off distances from a structure to be tested at a position free from defects. The point where the detected signals cross in the time domain is determined to establish a "lift-off point of intersection" at that particular point in time of the time domain signal. The amplitudes of subsequent time domain test signals are compared at that same point of time at which the calibration signals crossed to compensate for lift-off.

However, the intersection point may not be very precise and may drift when different size defects are detected. Furthermore, lift-off compensation is only achieved at a single point on the received signal such that only a limited amount of information is available from the time domain signal limiting defect analysis.

U.S. Pat. No. 5,391,988 discloses a method of detecting a flaw within a conductive object using eddy current testing. A ferrite core has a primary and a secondary coil wound upon it. A rectangular-wave current is supplied to the primary coil to induce a voltage of a pulse wave form in the secondary coil. The pulse duration of the induced voltage is measured at two separate time instances corresponding to two different threshold voltages. The effect of variations in the distance between the ferrite core and the conductive object (lift-off) are cancelled using a comparison of the two measured pulse durations.

U.S. Pat. No. 6,573,712 discloses an inspection device which has a driving section to adjust a position of an inspection probe to maintain a constant lift-off.

Making the right judgement about lift-off occurrence and related lift-off distance enables the removal of the component of the detected signal caused by lift-off that masks the defect signal, so that the defect information may be recovered to provide reliable detection results.

SUMMARY OF THE INVENTION

According to a first aspect of the present invention, there is provided a method for compensating for separation between an eddy current probe and a surface of a conductive specimen (lift-off), the method comprising obtaining at least one set of reference data by locating an eddy current probe at a defect free specimen area and at a known reference separation (lift-off) from a surface of the specimen, the probe being excited to generate eddy currents in the specimen and sensing a reference signal generated by the eddy currents produced in the conductive specimen at the known reference separation; and determining a gradient value of the sensed signal;

performing subsequent test measurements by locating the eddy current probe at an unknown separation (lift-off) from a surface of the specimen with the probe being excited to generate eddy currents and determining the corresponding gradient value of the subsequent test signals and compensating for the separation between the eddy current probe and the surface of the specimen (lift-off) in the test measurements by determining the difference between at least one reference signal and the test signal.

It has been found that the gradient of a sensed signal is indicative of the separation (lift-off) between the probe and the surface of the conductive material being tested. Embodiments of the present invention have been found to have the capability to provide precise and reliable lift-off compensation. Embodiments of the present invention also provide a complete lift-off compensated signal unlike many prior methods which only provide lift-off compensation at a single point along a time-varying signal. A complete signal is useful for subsequent signal analysis and processing to determine the nature and location of defects. Pulsed eddy currents are preferably generated.

Before sensing the reference and test signals, balancing may be performed by placing the probe on a defect free area with no lift-off and obtaining a balance signal which is then subtracted from all subsequent signals.

The largest magnitude gradient (regardless of whether it is a positive or a negative gradient) is preferably determined and used to perform the compensation. The largest magnitude gradient may be easily determined by a control system including a processor or computer for example which can determine a peak differential of the sensed time-varying signal. Consequently, the method of the present invention may be easily automated. The sensed signal is preferably smoothed, such as by being passed through a low pass filter, prior to determining the gradient to remove any spurious results produced by noise.

Compensation in the test measurements may involve obtaining a plurality of sets of reference data, each at a different known separation between the probe and the surface of the specimen. The set of reference data with the closest gradient to the test signal may then be selected and the difference determined between the selected reference signal and the test signal. Alternatively or additionally reference data may be interpolated from one or more reference sets of data. The data relating to the reference signal or test signal may be multiplied by a factor dependent upon a ratio of the sizes of the test and reference signals.

According to a second aspect of the present invention there is provided an eddy current inspection device comprising an eddy current probe and a processing means arranged to perform the method of the first aspect of the present invention.

BRIEF DESCRIPTION OF THE DRAWINGS

The invention will now be described, by way of example only, with reference to the accompanying drawings in which:

FIG. 4b shows the differential of the signals presented in FIG. 4a;

DETAILED DESCRIPTION OF AN EMBODIMENT OF THE PRESENT INVENTION

Figure 1:
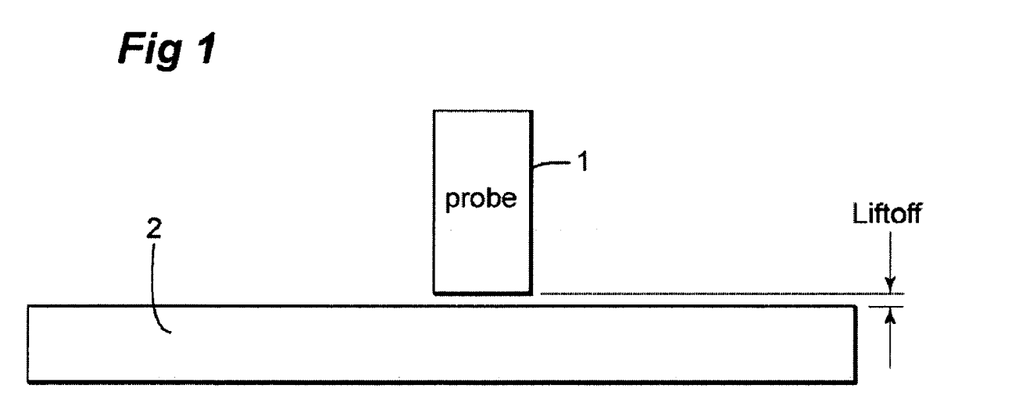
FIG. 1 illustrates the separation (lift-off) between a probe and a surface of a sample.

FIG. 1 illustrates the separation known as lift-off between a probe 1 and the surface of a specimen 2 to be inspected.

Figure 2:
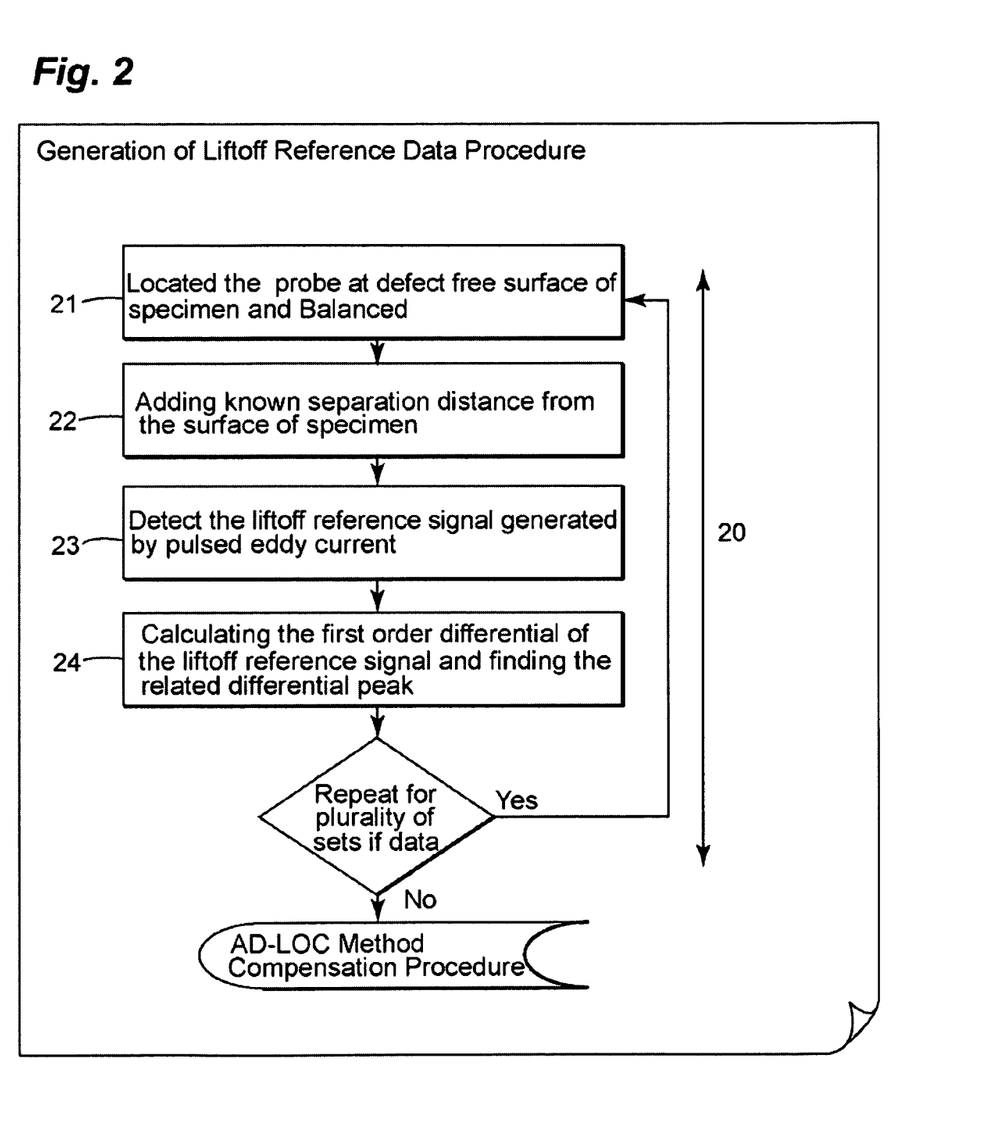
FIG. 2 shows a flow diagram illustrating a method of performing an embodiment of the invention.

FIG. 2 is a flow diagram 10 illustrating an example of a method of performing the present invention. The flow diagram consists of a first portion 20 for generating reference data and a second portion 30 for generating compensated test data.

As illustrated in FIG. 2 at step 21, the probe is preferably balanced by being placed on a defect free area with no lift-off to obtain a balance signal to be subtracted from all subsequent signals. At step 22 the probe is located a known reference separation (lift-off) from the surface of a sample. The probe is preferably located over a portion of the sample which is substantially free from defects. Any suitable eddy current probe as is well known in the art may be used, such as an absolute probe, a differential probe, a reflection probe, an unshielded probe, a shielded probe or combinations of the above in single, multiple or array configurations using coil or electronic sensors. In this example a probe with an integral transmitter coil and receiver array is used. The receiver array typically has 16 or 32 sensors as is well known in the art. However, a probe with a separate transmitter and receiver may be used if desired. The probe may be located at a known lift-off from the surface of the specimen by placing a shim (usually non-conductive) of known thickness between the probe and a non-defective part of the sample.

At step 23 the probe is excited to generate eddy currents in the surface of the sample and a reference signal generated by the eddy currents is detected by the probe. The transmitter coil is excited, for example with a square-wave current, to generate a wide band of frequencies so that defects at many depths in the specimen may be detected.

At step 24 the gradient of the reference signal is determined. Preferably the maximum gradient (regardless of whether the gradient is positive or negative) of the reference signal is determined. An eddy current inspection device in accordance with the present invention would have a processing means such as a microprocessor which could determine the gradient by calculating the first order differential of the reference signal. The largest magnitude of the gradient of the test signal would be the peak value of the first order differential. At least one of the detected reference signal or determined gradient or differential is smoothed for example by Gaussian smoothing or by being passed through a low pass filter in order to remove any spikes which may be caused by noise and which could generate erroneous values. The detected reference signal and its associated peak gradient or differential are stored together in a memory means associated with the processor.

Depending upon how many sets of reference signals and associated gradients are required, steps 21 to 24 are repeated as many times as necessary. It has been found that the use of more sets of reference signals provides more precise results. If steps 21 to 24 are repeated then a different shim (usually non-conductive) of another known thickness is placed between the probe and a non-defective part of the sample to make measurements at this second known lift-off. If multiple sets of reference signals are generated then the gradient for each of the generated reference signals could either be determined individually after each reference signal is obtained or all of the gradients could be determined together after all of the reference signals have been detected.

When a suitable number of reference signals and associated gradients have been determined the method may be used to generate test data in order to detect any defects. The test data may be compensated for lift-off. At step 31 the probe may be located over the specimen. However, in contrast to the probe's use to generate reference data as in steps 21 to 24 above, in this instance it does not matter what level of separation exists between the sample and the probe. In practice the probe is likely to be passed over sections of a structure to be tested such as an aircraft panel or a pipeline component and the lift-off is likely to vary as the probe passes over the structure, due to for example variations in the thickness of paint work, coatings and insulation, due to the probe encountering surface features such as rivets etc and due to variations in pressure applied to the probe by the operator.

At step 32 the signal generated by the eddy currents in the specimen are sensed using the receiver in the probe.

At step 33 the gradient of the test signal is determined, in this example by calculating the first order differential and determining its differential peak. As in step 23 when generating reference data above, the largest magnitude gradient of the test signal is preferably determined by calculating the peak differential of the test signal.

At step 34 the test signal is compensated to reduce or remove the effects of lift-off. This is performed by subtracting weighted lift-off reference data relating to a generated reference signal from the data for the test signal. If a plurality of reference signals were generated, the reference signal with the most similar gradient peak or closest peak differential to that of the test signal would be identified, and indexed as the current lift-off appearance and the corresponding weighted identified reference signal used as the signal which is subtracted from the test signal. The maximum gradient or peak differentials may be compared by any suitable method such as the nearest distance rule as is well known to those skilled in the art. Alternatively or additionally data for a reference signal may be interpolated to produce a more suitable set of reference data to be subtracted from the data for the test signal. Interpolation may be helpful, for example when the slope of a test signal is found to lie substantially midway between the slopes of two reference signals or if only a single reference signal is available. The reference signal may be multiplied by a compensation ratio derived from a ratio of the test signal and the corresponding reference signal to compensate for any difference in sizes of the test and reference signals. In this example step 34 is preceded by a series of steps 34a to 34d to determine whether the lift-off phenomena is present for the generated signals and if so to switch on the compensation function and select a reference signal. If desired lift-off compensation may be switched off at step 34e. The compensation procedure is repeated at step 34f until all data has been compensated and imaging of the data is then performed at step 34g.

Figure 3:
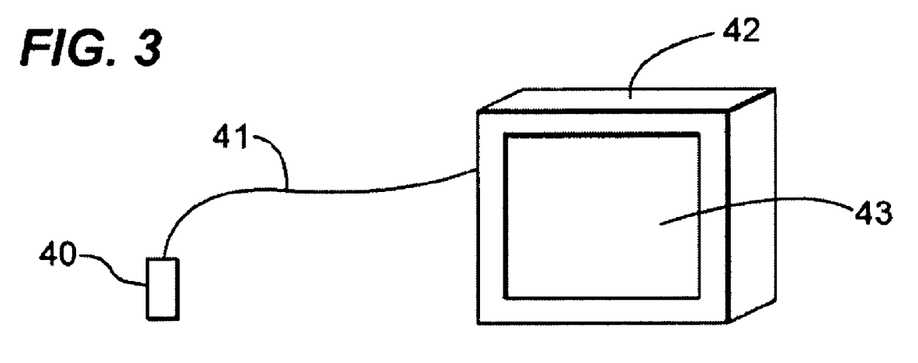
FIG. 3 illustrates a pulsed eddy current inspection device.

FIG. 3 illustrates a pulsed eddy current inspection device suitable for use to perform the present invention. The device includes a probe 40 as described above. The probe 40 in this example has an array of sensors. The probe 40 is connected via connector 41 to a processing and display device 42. The processing and display device 42 has a processor, such as a microprocessor and a memory to store signals and perform appropriate processing such as determination of peak differentials, performance of compensation and storage of signals with associated peak differentials. The device 42 has a display means 43 to display results to a user.

The device 42 may perform an automatic differential lift-off compensation process as described below:

1) First, a number (K) of lift-off reference signals Lo_Ref (k), each at a predetermined lift-off of the probe 40 from a sample is collected. This is the reference signal set.
   Lift-Off Reference Set: {Lo_Ref(k)} k=1, 2, ..., K
   For example: lift-off distance: 5 mil (0.127 mm), 10 mil (0.254 mm), 15 mils (0.381 mm) and 20 mils (0.508 mm) are used to produce four Lift-off reference signals. K=1, 2, 3, 4
2) After that, all the known lift-off reference signals first order differentials are calculated to find their peak values DPv_Lo_Ref(k), where k=1, 2, ..., K.

In this example, the differential operator is a First order Differential, the Smoothing Operator is Gaussian Smoothing and the Differential Peak Values are termed: DPv_Lo_Ref Set
3) Next a lift-off reference book set is defined which is composed of the lift-off reference signal Lo_Ref(k) and its corresponding differential peak values DPv_Lo_Ref (k) where k=1, 2, ..., K
   LO_Ref_Book={Lift-Off Reference Set DPv_Lo_Ref Set}
   ={Lo_Ref(k), DPv_Lo_Ref(k)}
   k=1, 2, ..., K
4) Then for each individual test signal with unknown defects and unknown lift-off type, the following is performed:
   a) Calculate the differential peak value for the test signal—DPv_test.
   b) Compare the current DPv_test with DPv_Lo_Ref Set by the nearest distance rule to find the most similar DPv_Lo_Ref(k) and obtain the lift-off class index k.
   c) According to the lift-off class index k, we learn the type of the lift-off embedded in the test signal, so that we are able to choose the right corresponding lift-off reference signal Lo_Ref(k) in the later compensation procedure.
5) Finally, with Lo_Ref(k), by using a compensation formula automatic lift-off compensation is realised. The compensation formula comprises determining the difference between the appropriate reference signal and the test signal.

A compensation ratio is preferably also calculated according to the following expression:

Ratio=DPv_test/DPv_Lo_Ref

The compensation ratio may then be included in the compensation formula

Auto_Comp=Sig_test−Ratio*Sig_LO_Ref(k)

where Sig_test is the test signal and Sig_LO_Ref(k) is the appropriate reference signal.

Figure 4A:
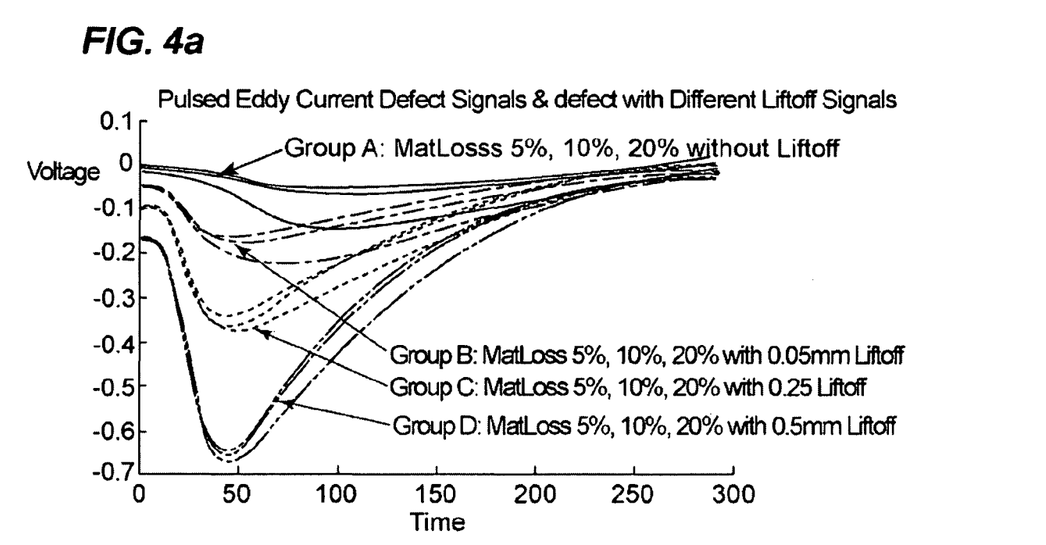
FIG. 4a shows a series of detected pulsed eddy current signals obtained from a specimen without lift-off and at a number of different lift-offs.

FIG. 4a shows a series of detected pulsed eddy current signals obtained from a specimen without lift-off (Group A) and with the probe at a lift-off of 0.05 mm (Group B), with a lift-off of 0.25 mm (Group C) and with a lift-off of 0.5 mm (Group D). Groups A, B, C and D each contain signals for defects that are about 5%, 10% and 20% of total specimen thickness material loss. As can clearly be seen from FIG. 4a, the gradient of the pulsed eddy current signals is mainly affected by the lift-off distance whereas a variation in defect size within each individual group has far less of an effect. Therefore, in FIG. 4a, the pulsed eddy current signals relating to different defect sizes but with the same lift-off distance were clustered into the same group of pulsed eddy current signals which is mainly decided by the lift-off distance.

Figure 4B:
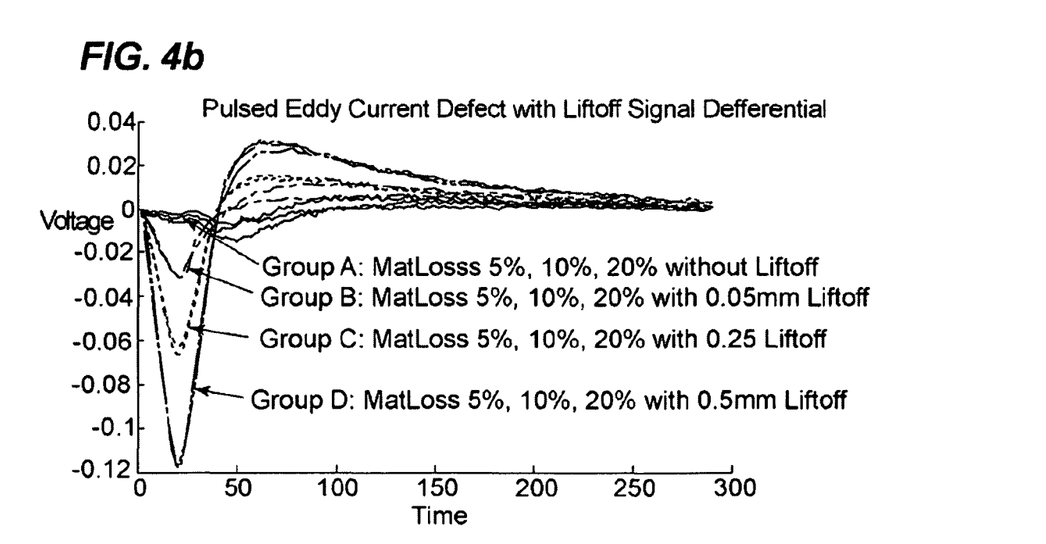

FIG. 4b shows the differentials of the signals presented in FIG. 4a. The differentials of the pulsed eddy current signals with different defects but with the same lift-off distance were not only clustered into the same group dependent upon the lift-off distance, but also provided very close differential peak values. From this it can be seen that the differential peak values are clearly indicative of the lift-off present in that pulsed eddy current signal. The lift-off features are extracted and used to calculate the compensation ratio parameter to perform automatic lift-off compensation.

Figure 4C:
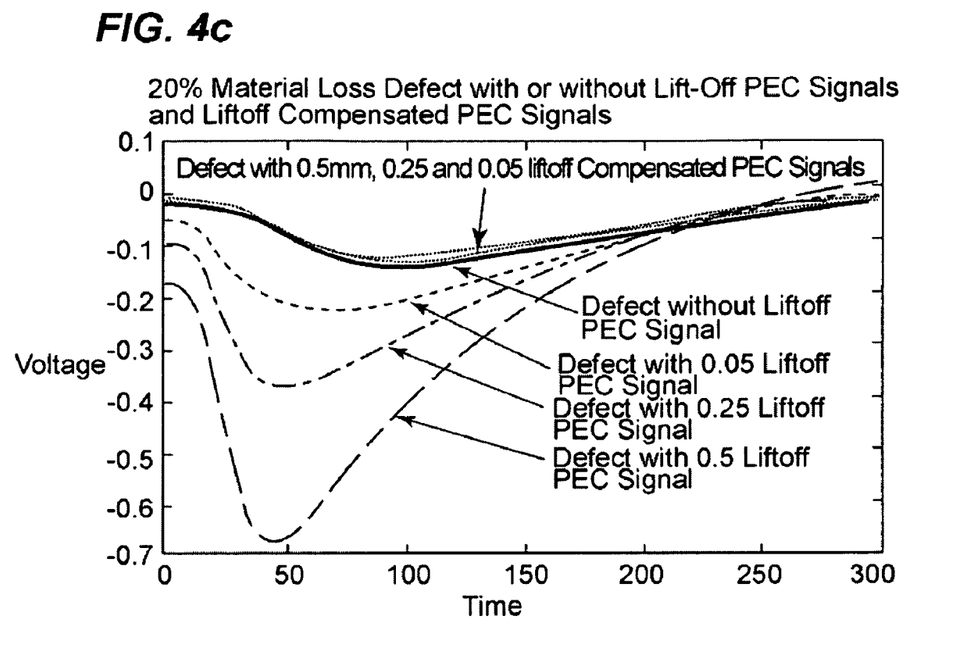
FIG. 4c shows pulsed eddy current signals from a 20% defect before and after they have been compensated for lift-off.

FIG. 4c illustrates the effect of variable lift-off pulsed eddy current compensation in accordance with an embodiment of the present invention. An ideal pulsed eddy current signal for a specimen with a defect of 20% of the total specimen thickness material loss with the probe carefully positioned so that there was no lift-off between the probe and the surface of the specimen is indicated in FIG. 4c by the thick solid line. This is the ideal signal that would be obtained without the effect of lift-off. Pulsed eddy current signals obtained from the 20% defect of the specimen with 0.05 mm, 0.25 mm and 0.5 mm lift-off distances are also shown in FIG. 4c by the respective indicated dashed lines. The corresponding lift-off compensated pulsed eddy current signals are shown in close dashed lines which partly overlap the ideal signal obtained without lift-off. The effectiveness of the lift-off compensation of embodiments of the present invention is clearly illustrated in FIG. 4c by how closely the lift-off compensated signals follow or even overlie the ideal signals obtained without lift-off.

Figure 5A:
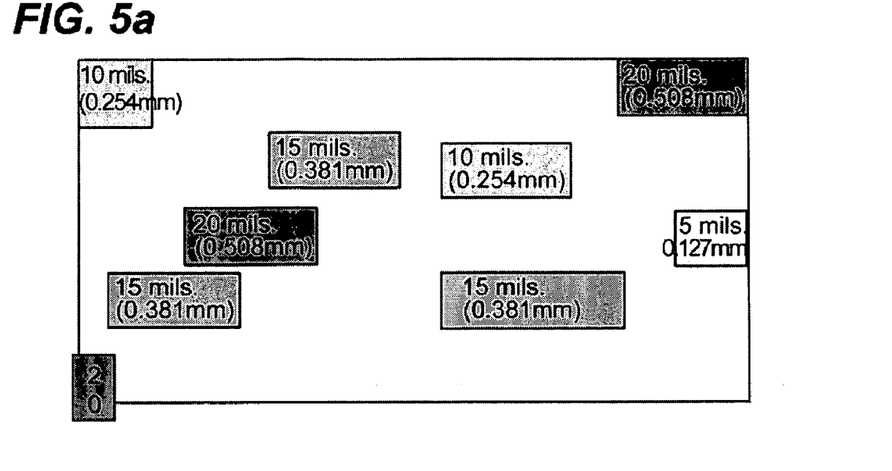
FIG. 5a shows variable lift-off distances and locations used in a pulsed eddy current test scan.
Figure 5B:
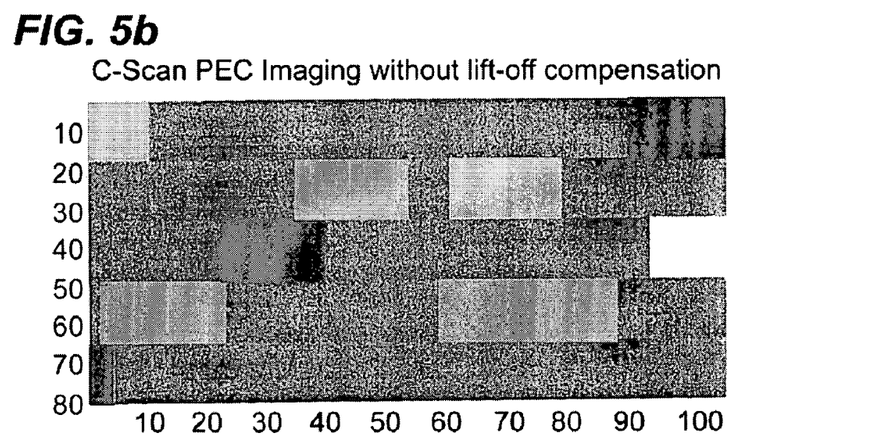
FIG. 5b shows a pulsed eddy current image of an inspection C-scan without lift-off compensation and FIG. 5c shows the inspection C-scan of FIG. 5b with lift-off compensation according to an embodiment of the present invention applied.
Figure 5C:
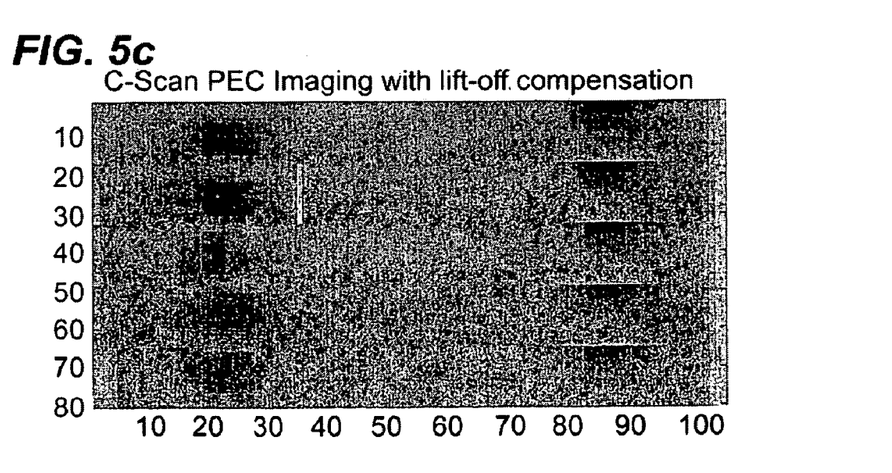

FIGS. 5a, 5b and 5c illustrate lift-off compensation of an embodiment of the present invention performed on a pulsed eddy current C-scan image.

FIG. 5a illustrates the lift-off distances and their locations in the pulsed eddy current C-scan. Different lift-off distances, namely 0 mm, 0.127 mm, 0.254 mm, 0.381 mm and 0.508 mm are presented by different shades in the monochrome image of FIG. 5a but could also be illustrated by different colours.

FIG. 5b shows a pulsed eddy current image of an inspection scan as may be seen on the display means 43 of the device 42 shown in FIG. 3. The scan image shows a pulsed eddy current image in which different shades or colours indicate different levels of material loss. A chart indicating the percentage level of material loss indicated by a particular shade or colour may be provided adjacent to the pulsed eddy current C-scan image. The pulsed eddy current C-scan image indicates the location of defects consisting of material loss presented as different shades or colours in a position on the C-scan image corresponding to the actual location of the defect in the structure being tested. The image shown in FIG. 5b indicates typical data that may be acquired by passing a probe 40 as shown in FIG. 3 over a surface of a structure to be tested. A number of "patches" are shown which are due to lift-off of the probe 40 in the measurement at that point during use as indicated by FIG. 5a. As can be seen from the scanned image of FIG. 5a, the patches caused by lift-off incurred at those points make the C-scan image rather unclear such that actual defects may be difficult to identify.

In contrast, FIG. 5c shows the Pulsed Eddy Current C-scan Image of FIG. 5b after lift-off compensation has been applied in accordance with an embodiment of the present invention. As can be seen, the defects at positions 20 and 90 on the x-axis can be seen much more clearly than in the C-scan Image in FIG. 5b. The defects are now so clear that information about the shapes of the defects is clearly discernable. The presence and location of the defects is clearly seen after the lift-off effect has been removed. Thus far more precise defect information may be obtained.

Many variations may be made to the examples described above whilst still falling within the scope of the invention. For example any suitable eddy current probe may be used. The probe may have a transmitter and receiver provided integrally together within the probe body or the transmitter and receiver may be provided separately. The receiver may comprise one or more coils or sensors.

What is claimed is:

1. A method for compensating for the effect of separation between an eddy current probe and a surface of a conductive specimen being tested, the method comprising
   obtaining set of reference data by locating the eddy current probe at a substantially defect free area and a known reference separation from a surface of the specimen, the probe being excited to generate eddy currents in the specimen and sensing a time-varying reference signal generated by the eddy currents, the set of reference data containing the amplitude of the reference signal at one or more times
   determining a largest magnitude gradient value of the reference signal;
   obtaining a set of test data by locating the eddy current probe at an unknown separation from the surface of the specimen the probe being excited to generate eddy currents in the specimen and sensing a time-varying test signal generated by the eddy currents, the set of test data containing the amplitude of the test signal at one or more times;
   determining largest magnitude gradient value of the test signal
   calculating a compensation ratio, the compensation ratio being the largest magnitude gradient value of the test signal divided by the largest magnitude gradient value of the reference signal; and
   determining an amplitude of a compensated signal for one or more corresponding times in the sets of reference and test data by subtracting the amplitude of the reference signal multiplied by the compensation ratio from the amplitude of the test signal.

2. A method in accordance with claim 1, wherein a plurality of reference signals are sensed and a corresponding plurality of sets of reference data are obtained, each reference signal being generated by eddy currents generated by exciting the probe at different known reference separation from the surface of the specimen, wherein a largest magnitude gradient value is determined for each reference signal, and wherein the reference signal with the largest magnitude gradient value closest to the largest magnitude gradient value of the test signal is used to determine the compensation ratio and compensated signal amplitude.

3. A method in accordance with claim 2, wherein the largest magnitude gradient value for each reference signal is determined by the peak first order differential of each reference signal, and the largest magnitude gradient value for the test signal is determined by the peak first order differential of the test signal.

4. A method in accordance with claim 3, wherein at least one of the plurality of reference signal, the first order differential for the plurality of reference signals, or the peak first order differential for the plurality of reference signals is smoothed.

5. A method in accordance with claim 2, wherein the reference signal with the largest magnitude gradient value closest to the largest magnitude gradient value of the test signal is determined using the nearest distance rule.

6. A method in accordance with claim 2, wherein at least a portion of the data in the sets of reference data is interpolated.

7. A method in accordance with claim 1, wherein the step of determining an amplitude of a compensated signal determines the compensated signal amplitude for each time stored in the set of test data to determine a complete compensated signal.

8. A method in accordance with claim 1, wherein at least a portion of the data in the set of reference data is interpolated.

9. An eddy current inspection device comprising an eddy current probe and a processing means arranged to perform the method of claim 1.

10. An eddy current inspection device according to claim 9, wherein the probe is an absolute probe, a differential probe, a reflection probe, an unshielded probe, a shielded probe or any combination thereof in single, multiple or array configuration using coil or electronic sensors.

11. A method in accordance with claim 1, wherein the largest magnitude gradient value for the reference signal is determined by the peak first order differential of the reference signal, and the largest magnitude gradient value for the test signal is determined by the peak first order differential of the test signal.

12. A method in accordance with claim 1, wherein the amplitude of the reference signal, the amplitude of the test signal, and the amplitude of the compensated signal represent voltage.

\* \* \* \* \*

UNITED STATES PATENT AND TRADEMARK OFFICE
CERTIFICATE OF CORRECTION

| | | |
|---|---|---|
| PATENT NO. | : 8,008,913 B2 | Page 1 of 1 |
| APPLICATION NO. | : 12/134317 | |
| DATED | : August 30, 2011 | |
| INVENTOR(S) | : Qiao et al. | |

It is certified that error appears in the above-identified patent and that said Letters Patent is hereby corrected as shown below:

On the Title Pg, below Item "(65)",
insert -- (30) Foreign Application Priority Data
Dec. 6, 2007 (UK) ................... 0711349.1 --.

Signed and Sealed this
Third Day of January, 2012

David J. Kappos
*Director of the United States Patent and Trademark Office*